United States Patent [19]

Sekons

[11] Patent Number: 5,776,152
[45] Date of Patent: Jul. 7, 1998

[54] INTRACORPOREAL LIGATURE DEVICE

[76] Inventor: David H. Sekons, 41 Fifth Ave., New York, N.Y. 10003

[21] Appl. No.: 816,845

[22] Filed: Mar. 13, 1997

[51] Int. Cl.$^6$ ................................................. A61B 17/04
[52] U.S. Cl. ........................... 606/148; 606/139; 606/144
[58] Field of Search ................................ 606/139, 144, 606/148

[56] References Cited

U.S. PATENT DOCUMENTS

| | | |
|---|---|---|
| 5,037,433 | 8/1991 | Wilk et al. . |
| 5,144,961 | 9/1992 | Chen et al. ............... 606/148 |
| 5,250,054 | 10/1993 | Li . |
| 5,282,809 | 2/1994 | Kammerer et al. ....... 606/148 |
| 5,336,231 | 8/1994 | Adair . |
| 5,423,836 | 6/1995 | Brown ........................ 606/148 |
| 5,466,243 | 11/1995 | Schmieding et al. . |
| 5,480,405 | 1/1996 | Yoon .......................... 606/143 |
| 5,658,299 | 8/1997 | Hart ........................... 606/148 |
| 5,665,096 | 9/1997 | Yoon .......................... 606/148 |

FOREIGN PATENT DOCUMENTS 41 27 812 A1  2/1993  Germany .

*Primary Examiner*—Gary Jackson
*Attorney, Agent, or Firm*—Meltzer, Lippe, Goldstein, et al.

[57] ABSTRACT

An intracorporeal ligature tying device enables a surgeon to tie various types of knots within the body cavity of a patient during endoscopic surgery. The tying device comprises: (a) a needle holder having a longitudinal channel running though the length of the needle holder, the needle holder having a proximal end and a distal end; (b) a longitudinal groove located on an outside surface of the needle holder, the groove terminating at a location on the needle holder prior to the distal end of the needle holder, at least a final portion of the groove being covered; and (c) a wire located in the groove, the wire being made from a memory material. The wire is slidably positioned within the groove so that in a retracted position, the wire terminates in the covered portion of the groove, and in an advanced position, an end of the wire extends beyond the covered portion of the groove and forms a hook to aid in tying a ligature within a patient's body.

7 Claims, 9 Drawing Sheets

INTRACORPOREAL LIGATURE DEVICE

FIELD OF THE INVENTION

The present invention is directed to a surgical instrument and, more particularly, to an endoscopic ligature tying aid.

BACKGROUND OF THE INVENTION

Endoscopic surgery is surgery performed intracorporeally without requiring a large incision. Endoscopic surgery is typically performed by inserting a number of ports through small incisions in the patient's skin to access the surgical site with instruments passing through the ports. One of the ports receives an endoscope, which is a video camera-like device. The surgeon views the surgical site via the endoscope and performs the surgery by inserting surgical devices through the ports into the patient. This avoids having to "open up" the patient, resulting in less invasive surgery than conventional procedures.

One type of endoscopic surgery is laparoscopic surgery. In this type of surgery, typically 3–4 tubes are inserted through ports in a patient's cutaneous region of the skin. The tubes pass through several tissue and muscle layers, past the peritoneal membrane, which encloses the abdominal cavity, and into the abdominal cavity. One tube receives a laparoscope which is a type of endoscope. The other tubes receive other implements needed to carry out the laparoscopic surgery, e.g., needles, forceps, graspers, etc. The laparoscope provides a light source and may be connected to video equipment for displaying the surgical site on a TV monitor. The same tube may also receive an insufflator which inflates the abdominal cavity with $CO_2$ allowing the organs to be seen, and providing the surgeon with room to manipulate surgical instruments. Laparoscopic surgery is commonly used for many types of abdominal surgery and is also becoming increasingly common in other surgical areas, such as thoracic surgery. The invention is described herein illustratively with respect to laparoscopic surgery, but a person skilled in the art readily understands that the invention described may be used in other types of endoscopic surgery as well.

One difficulty f acing surgeons performing laparoscopic surgery is ligating through the ports. A surgeon may wish to tie knots during laparoscopic surgery for many reasons. For example, a surgeon may wish to close an incision made in an organ or to tie off a portion of an organ to be removed. Tying knots in ligatures during laparoscopic surgery is difficult because the surgeon can only access the surgical site through the ports.

This task is difficult for several reasons. The surgeon's access to the surgical site is limited to the access provided by the available ports. In a typical laparoscopic surgery, for example, the surgical site is quite distant from the surgeon's hands. For example, a standard grasping tool used for tying ligatures intracorporeally is 14 inches long. Thus, the surgeon's hands are more than a foot away from the surgical site. The surgeon has less control over and feel for the surgical instruments than if tying the sutures "hands on." E making a simple task much more difficult. Another reason is that the surgeon is not directly viewing the surgical site. Rather, the site is often viewed by watching a video monitor. The surgeon must replace hand-to-eye coordination with hand-to-video coordination. This places another link in the coordination chain, thereby making coordination more difficult. The camera also presents other difficulties, such as difficulties adapting to the depth of field presented, viewing angle, and limited camera frame size. Many surgeons have a great deal of difficultly acquiring the three dimensional perception and necessary skills that are required to tie ligatures during laparoscopic surgery.

Intracorporeal ligating and knot tying require a series of movements involving passing the ligature and needle from one surgical instrument to another. This series of passes is required for each "bite" of tissue in a simple running stitch. Even more difficult is knot tying the first and last passes of a run of continuous ligatures.

Several instruments and methods have been developed to tie ligatures during laparoscopic surgery. U.S. Pat. No. 5,037,433 (Wilk. et al.) discloses an endoscope and a needle having a spring bias construction tending to bend the needle. The surgeon passes the endoscopically introduced needle through tissue flaps. The needle and ligature are withdrawn through a port and a knot is tied outside the patient's body. Using a knot pushing device, the knot is pushed back into the body, securing the tissue flaps. This instrument and its method of use are not totally satisfactory. A long ligature length is required. This ligature length makes it difficult to tie continuous ligatures. Also, the instruments must be withdrawn from the ports to tie the knots, and therefore places the patient at a higher risk of infection since the removal of surgical instruments from the body subjects them to outside contaminants.

DE-OS 41 27 812 (Storz GmbH and Co.) discloses a needle holder for use in endoscopic surgical operations. The instrument comprises a tubular shaft with two jaws and a rigid loop at one end of the instrument. To tie a knot with the instrument, one end of a ligature is grasped by the jaws and the other end is passed through the loop. Using handles which pass through the shaft and are attached to the jaws, the jaws can be manipulated by the handles to form a knot in the thread. However, the knot which is made by this instrument is not a surgical knot, as preferred by most surgeons performing endoscopic surgery. The instrument disclosed in this instrument cannot tie a true surgeon's knot because the loop is fixed to the shaft and cannot rotate around the ligature in two directions. Thus, it cannot make the final locking throw in the opposite direction.

U.S. Pat. No. 5,250,054 (Li) discloses another kind of intracorporeal ligature device. This patent discloses an instrument comprising an outer sheath having a flexible intermediate section, and an inner rod which is movable relative to the outer sheath. The inner rod also has a flexible intermediate portion, and a crochet-type hook. By suitable sliding of the inner rod into one of three positions and suitable manipulation of a suture, a knot can be tied. This instrument is complicated in design and expensive to manufacture. Moreover, it requires extensive manipulation to tie the knot.

U.S. Pat. No. 5,336,231 (Adair) discloses a laparoscopic fixation, repair and ligation suture device. This multipurpose device comprises an elongated body with several passageways or channels including a central suture passageway through which a ligature with an already tied slip knot is passed into the body. Other instruments can be passed through the other channels in the body, such as an electrosurgical wire for cauterizing a ligated portion, or a hollow carrier device with a hook portion. The carrier device is loaded with a suture and is slipped around a blood vessel grasped by the hook. The end of the ligature is then grasped and pulled through the loop of a slip knot in the ligature. Here too, the instrument is complicated and expensive to manufacture, and also requires extensive manipulation.

Presently, there remains a need for a simple device which is inexpensive to manufacture and will allow a surgeon to tie a knot inside the body that overcomes the shortcomings of the instruments discussed above. The device should be able to aid in tying knots quickly and securely.

SUMMARY OF THE INVENTION

These objects are achieved by an intracorporeal ligature device according to the present invention. The device allows a ligature to be tied inside the body cavity with much greater ease than was previously possible. At the same time, the intracorporeal ligature device of the present invention is simple and inexpensive to manufacture. The free rotation of the device allows the ligature to be looped in two directions, enabling a surgeon's knot to be easily made.

The intracorporeal ligature device of the present invention comprises a hollow needle holder having a tapered distal end; a groove or channel running longitudinally down the exterior surface of the hollow needle holder and terminating about 3 cm before the distal end of the hollow needle holder, the groove being partially covered; and a wire made from a memory material located in the groove so that it is capable of curling when it is advanced towards the distal end of the hollow needle holder and emerges from the covered portion of the groove. This device can be used with a surgical ligature positioned within the hollow needle holder and a surgical needle attached directly to the end of the ligature extending from the distal end of the hollow needle holding device. The surgical needle is grasped by a pair of graspers and, together with the ligature is pulled away from the needle holder. The wire having a memory to curl is advanced toward the distal end of the hollow needle holder which causes the wire to emerge from the portion of the covered groove. Once the wire emerges it subsequently curls to form a hook. The hook is then used to hold a ligature so that a knot may be tied inside the body.

In another embodiment of the invention, the wire having a memory is replaced by a system using a hook attached to the surface of the hollow needle holder by a hinge. A wire runs along the surface of the hollow needle holder or in a groove or channel and attaches to the hook. When the wire is retracted towards the proximal end of the device, the hook will pivot away from the surface of the hollow needle holder about the hinge. When the wire is advanced towards the distal end of the device, the hook remains flush to the surface of the hollow needle holder. This embodiment of the intracorporeal ligature tying device is used in essentially the same way as the procedure described above except that a hook attached to the outside surface of the hollow needle holder by a hinge replaces the hook formed by the semi-rigid wire. As above, the hook is used to hold a ligature when tying a knot inside the body.

DETAILED DESCRIPTION OF PREFERRED EMBODIMENTS

Figure 1:
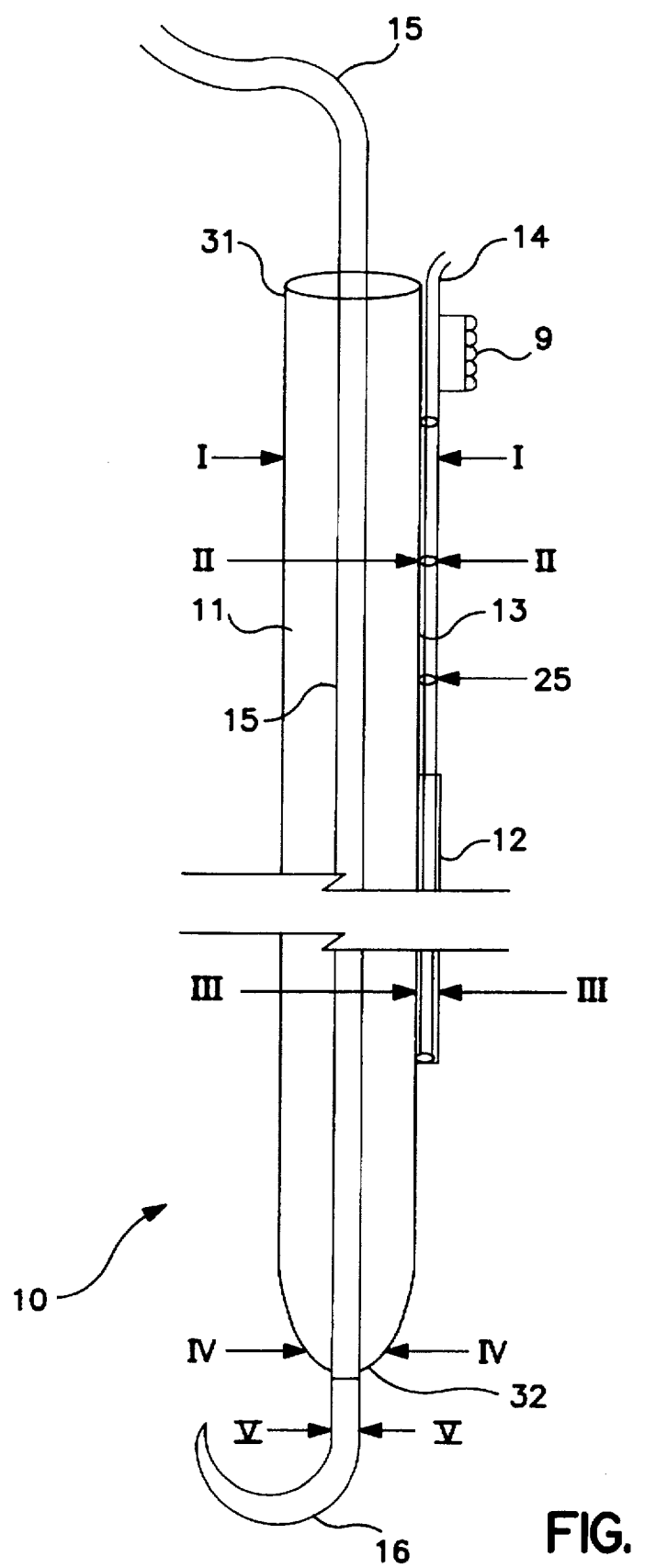
FIG. 1 is a partial side elevational view of the inventive intracorporeal ligature device.

Referring to FIG. 1, intracorporeal ligature device (10) comprises a hollow needle holder (11) having a proximal end (31) and a distal end (32). An open groove (13) runs longitudinally on the outer surface of the hollow needle holder (11) terminating 1-3 cm before the distal end (32). The open groove (13) is partially covered (12) from about the mid section of the hollow needle holder (11) to the end of open groove (13). A semi-rigid wire (14) runs within the open groove (13), through the covered portion (12) of groove (13), and terminates at the edge of the covered portion (12). The semi-rigid wire (14) is made of a memory material, such as a plastic material, that curls to produce a hook when unrestricted. A push button (9) is attached to an end of semi-rigid wire (14). When the semi-rigid wire (14) is advanced towards the distal end (32) of the hollow needle holder (11) by means of push button (9), it emerges from the covered portion (12) of groove (13). Once unrestricted, the semi-rigid wire (14) curls to produce hook (26). See, e.g., FIG. 7.

A ligature (15) may be pre-loaded within the lumen of the hollow needle holder (11), starting at the proximal end (31), and terminating at the distal end (32). The ligature (15) can be attached to surgical needle (16), which when pre-loaded in the hollow needle holder (11), will emerge from the distal end (32) of the hollow needle holder (11). The hollow needle holder can be used to maneuver the needle (16), attached to ligature (15) through the tissues which are to be ligated.

A needle grasper (see FIG. 8A), positioned at the surgical site through another port, is used to complete the pass through the two opposing tissues. Once the ligature (15) is completely through both tissues, the ligature is then laid to rest on the outer surface of the hollow needle holder (11).

At this point, push button (9), attached to semi-rigid wire (14), is advanced towards the distal end (32) of hollow needle holder (11), whereby the semi-rigid wire (14) exits from the covered portion (12) of groove (13). The semi-rigid wire (14), once unrestricted, curls to produce a hook (26). The hollow needle holder (11) is then rotated so that the ligature is positioned within the hook (26). Once the ligature (15) is position within hook (26), a triangle is formed between the hollow needle holder (11), the portion of the ligature entering the tissue and the portion of the ligature (15) exiting the tissue. The needle grasper can then be used to maneuver the ligature (15) through the formed triangle to complete the ligation steps. This procedure can be repeated to produce multiple throws.

Figure 2:
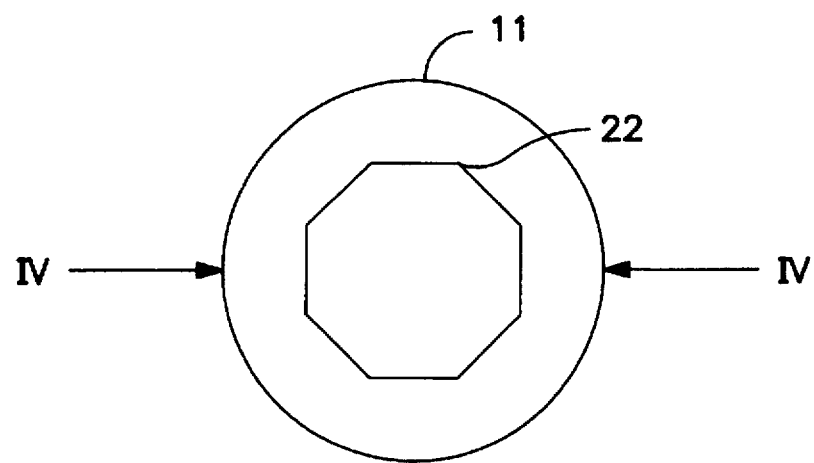
FIG. 2 is a cross section of the tapered end at point IV—IV, of the device of FIG. 1.
Figure 3:
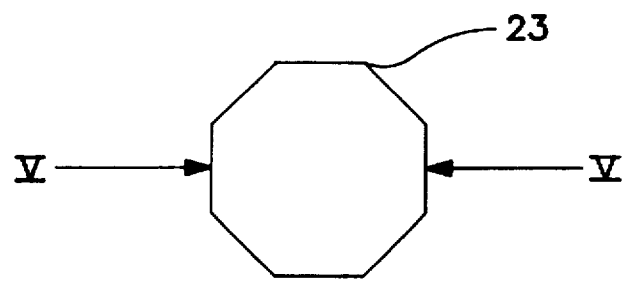
FIG. 3 is a cross section of a needle at point V—V, held by the inventive device of FIG. 1.

As shown in the cross-section of FIG. 2, at point (I), the distal end (32) of the hollow needle holder (11) has a tapered portion, which is designed to securely hold needle (16) in place. The inner wall (22) of the distal end (32) of the hollow needle holder (11) is polygonal in shape. As shown in FIG. 3, the shank portion of needle (16) has a polygonal shape complementary to the polygonal shape of inner wall (22) at point (I). This allows the needle to be secured into the tapered portion (I) of the hollow needle holder (11). Securing the needle (16) in place makes it easier for the surgeon to pass the needle (16) through tissue when suturing inside the body.

Figure 4:
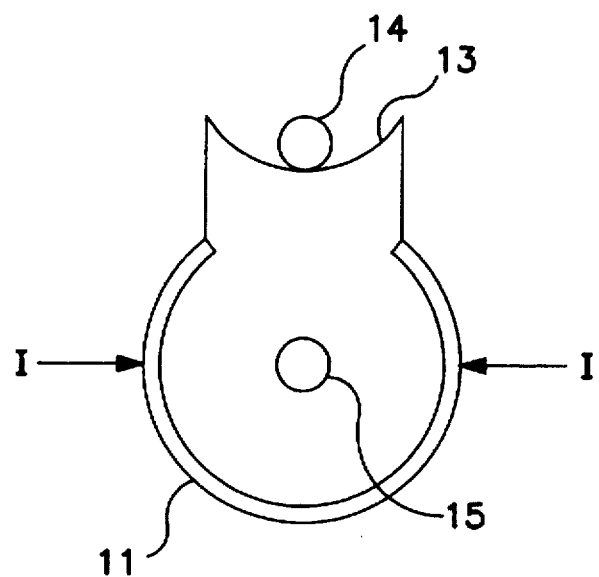
FIG. 4 is a cross section of the proximal end at point I—I, of the inventive device of FIG. 1, showing the bridged portion of the uncovered groove.

FIG. 4 shows a cross-section of the hollow needle holder (11) at point (I), including the uncovered portion of the groove (13), and the semi-rigid wire (14). Upon activation of push button (9), the semi-rigid wire (14), positioned within groove (13), can be advanced towards the distal end (32) of the hollow needle holder (11) thereby causing the semi-rigid wire (14) to emerge from the covered portion (12) of the groove (13). The push button (9) can also be used to retract the semi-rigid wire (14) back into the covered portion (12) of the groove (13).

Figure 5:
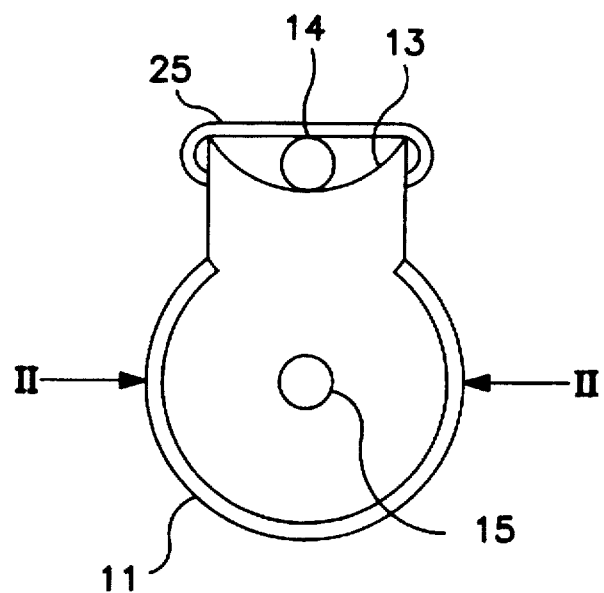
FIG. 5 is a cross section of the midsection at point II—II, of the inventive device of FIG. 1.

As shown in FIG. 5, at point (II), periodically positioned across the uncovered portion of the groove (13) are bridges (25), which maintain the semi-rigid wire (14) in an uncurled orientation. A plurality of bridges positioned periodically along the semi-rigid wire (14) restrain the semi-rigid wire (14) within groove (13) and prevent the semi-rigid wire (14) from curling.

Figure 6:
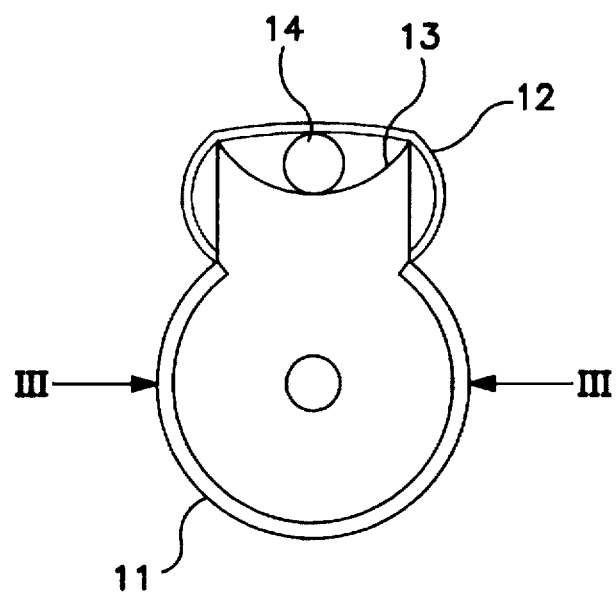
FIG. 6 is a cross section of the device of FIG. 1 at point III—III, showing the covered groove.
Figure 7:
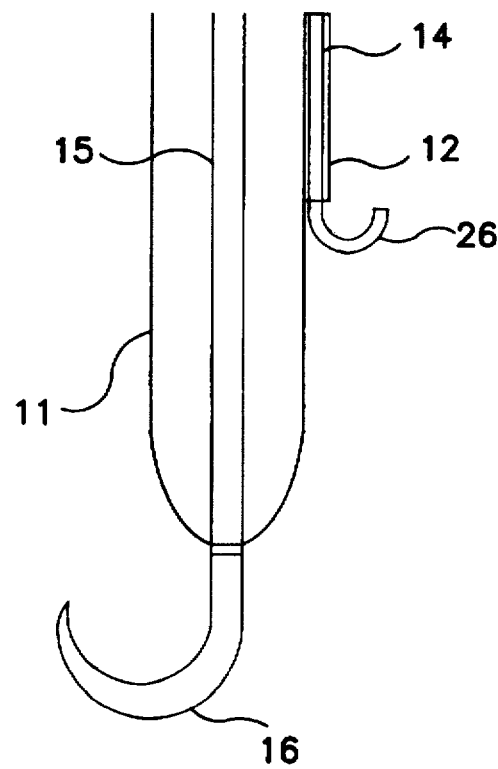
FIG. 7 is a partial side elevational view of the device of FIG. 1, showing the wire in the unrestricted position (curled).

FIG. 6, at point (III), shows the covered portion (12) of the open groove (13) at distal end (32) of the hollow needle holder (11). As discussed above, this covering maintains the semi-rigid wire (14) in an uncurled orientation by restraining the semi-rigid wire (14) within the groove (13). When hook (26) is required to aid in holding the ligature, the semi-rigid wire (14) is advanced towards the distal end (32) of hollow needle holder (11) to emerge out from under the covered portion (12) of the groove (13). Once unrestricted, semi-rigid wire (14) curls to form hook (26) as shown in FIG. 7.

Figure 9:
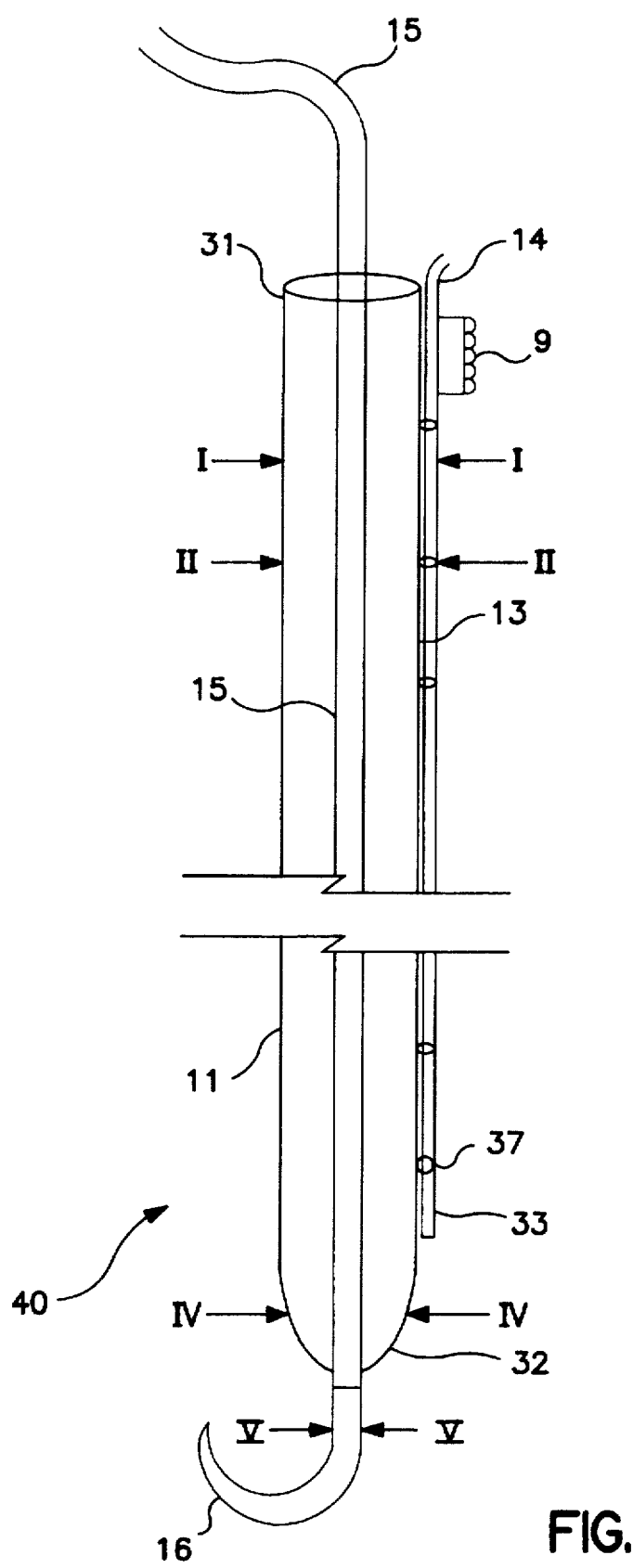
FIG. 9 is a partial side elevational view of another embodiment of the device wherein a hook is attached to the device by a hinge.

Another preferred embodiment is illustrated in FIG. 9. Device (40) is shown having a hook (33) attached to the device (40) by the hinge (34). Device (40) is used in a same way as the first embodiment except that, when the semi-rigid wire (14) is advanced or retracted it causes the hook (33) to pivot about the hinge (37). For example, when the semi-rigid wire (14) is retracted towards the proximal end (31) of the device (40), the hook (33) is pulled away form the outside surface of the device (40). When the semi-rigid wire (14) is advanced towards the distal end (32) of the device (40), the hook (33) remains flush against the surface of the device (40).

The hook (33) is used to hold the ligature in a stationary position so that the grasper (27) can be used to maneuver the needle (16) to complete the surgical knot.

Figure 8A:
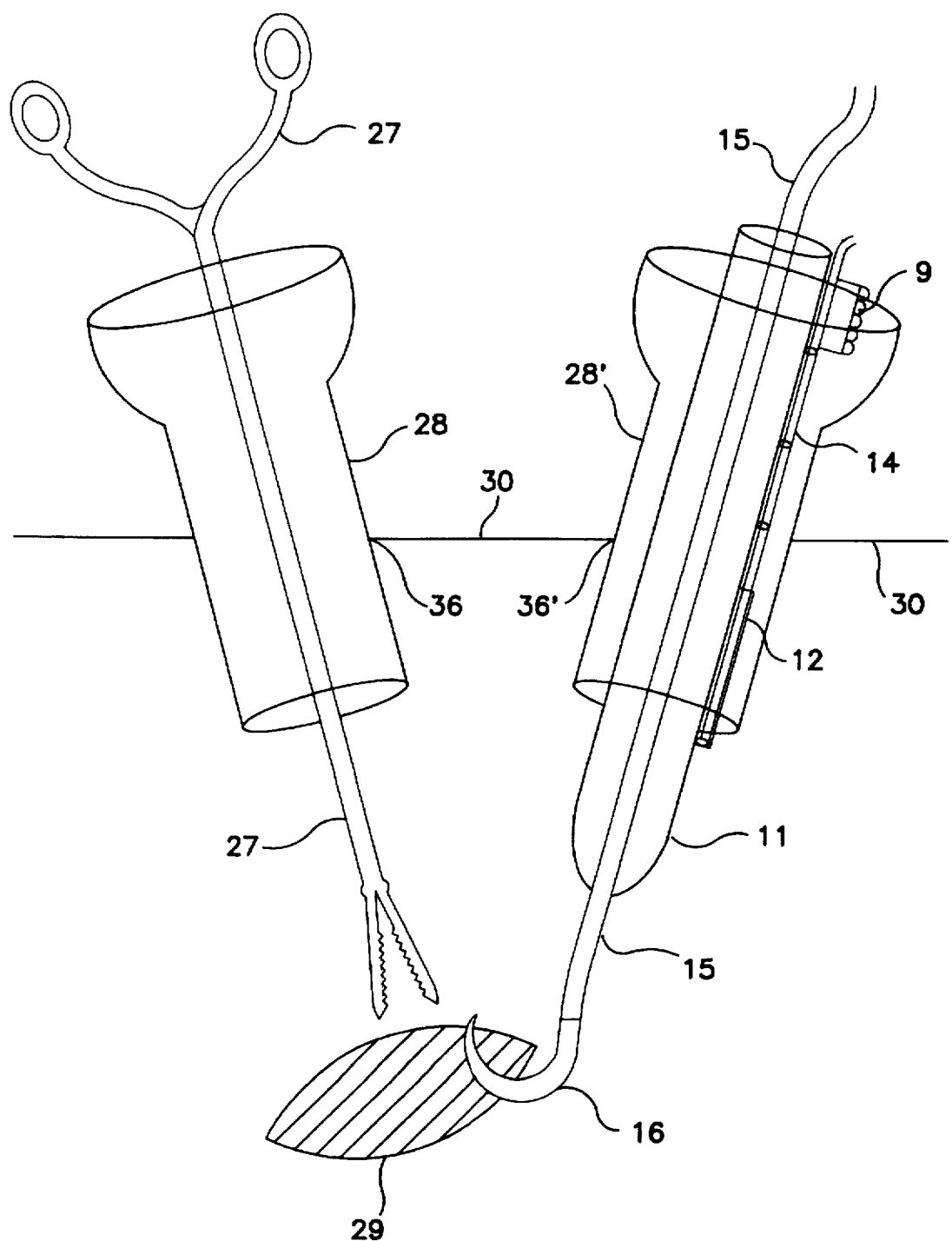
FIGS. 8A through 8F are schematic views showing successive steps in the operation of the device.
Figure 8B:
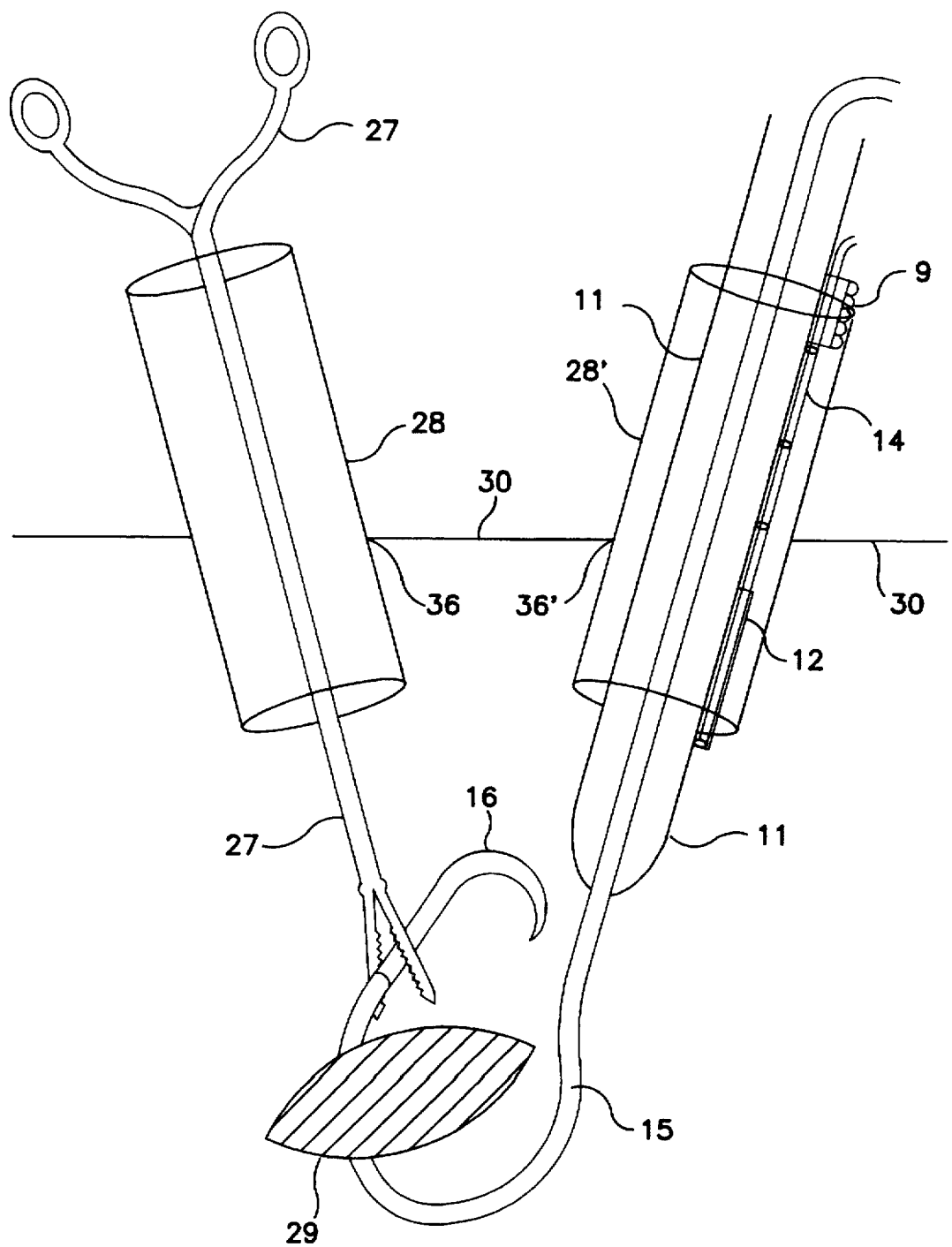

The use of the inventive device may be explained by reference to FIGS. 8A–8F. As shown in FIG. 8A, two endoscopic tubes (28) and (28'), are inserted into two ports (36, 36'), which penetrate the patient's skin (30). Endoscopic tube (28) is used to allow a needle grasping device (27) to gain access to the surgical site. The ligature tying device (10) gains access to the surgical site through tube (28'). When the device (10) enters the body cavity through the endoscopic tubes (28'), a needle (16) may be loosely attached to a pre-loaded ligature (15) within the device (10). The needle (16) is allowed to dangle from the distal end (32) of the hollow needle holder (11). This arrangement facilitates the passage through endoscopic tube (28'). When the device (10) is inside the body cavity, the ligature (15) is pulled taut and the needle (16), which has a shape complementary to the polygonal inside wall (22) of the distal end (32) of the hollow needle holder (11), fits securely.

Once the surgical site is located, the device (10) can be used to maneuver the needle through a tissue (29). A grasper (27) is introduced into the surgical site, through port (28), so that it is close enough to gain access to the surgical site. As illustrated in FIG. 8A, the rigid hollow needle holder (11) can be used to maneuver the needle (16) into a tissue (29). Once the needle (16) pierces tissue (29), the jaws of grasper (27) are used to pull the needle (16) completely through tissue (29). See FIG. 8B.

Figure 8C:
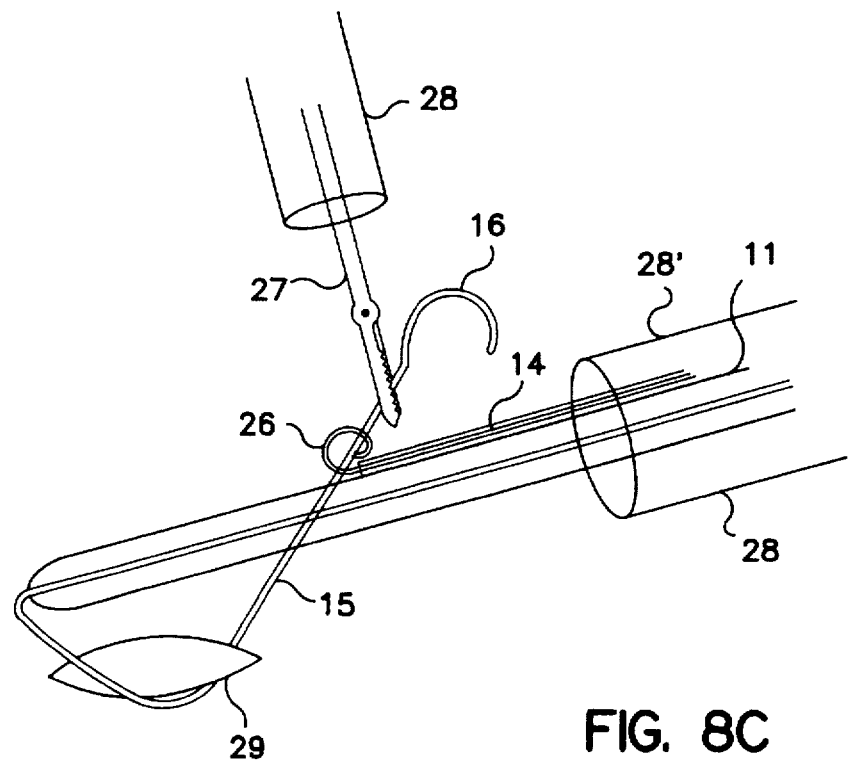

After the needle (16) is through the tissue, the semi-rigid wire (14) is advanced towards the distal end (32) of the hollow needle holder (11). Once advanced, the semi-rigid wire (14) emerges from the covered portion (12) of groove (13). As shown in FIG. 8C, the unrestricted semi-rigid wire (14) that emerges from the covered portion (12) of groove (13), curls to form a curled hook (26). The ligature (15) is then draped over the distal end of the hollow needle holder (11).

Figure 8D:
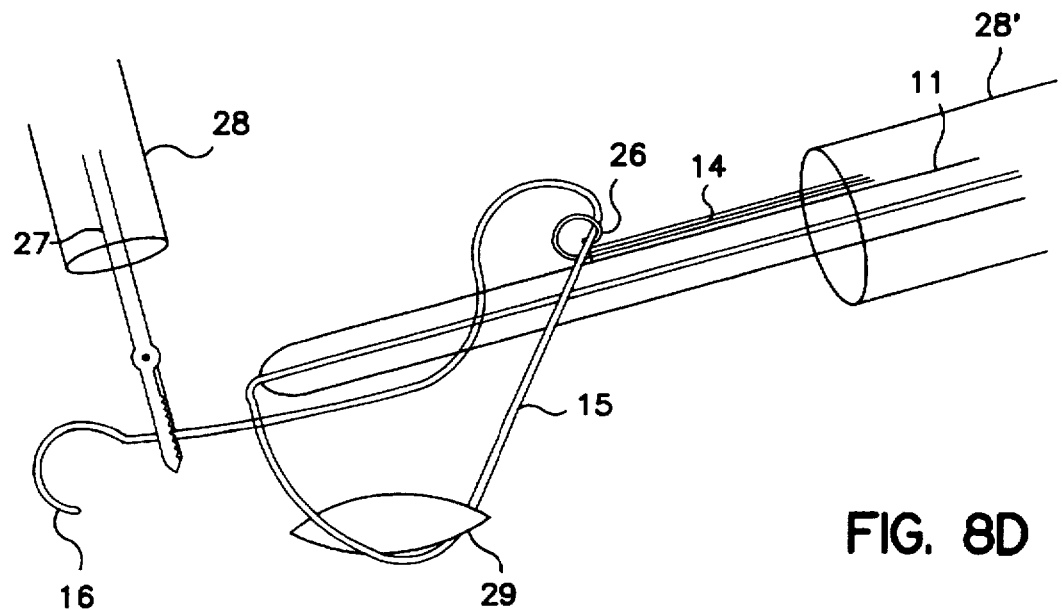
Figure 8E:
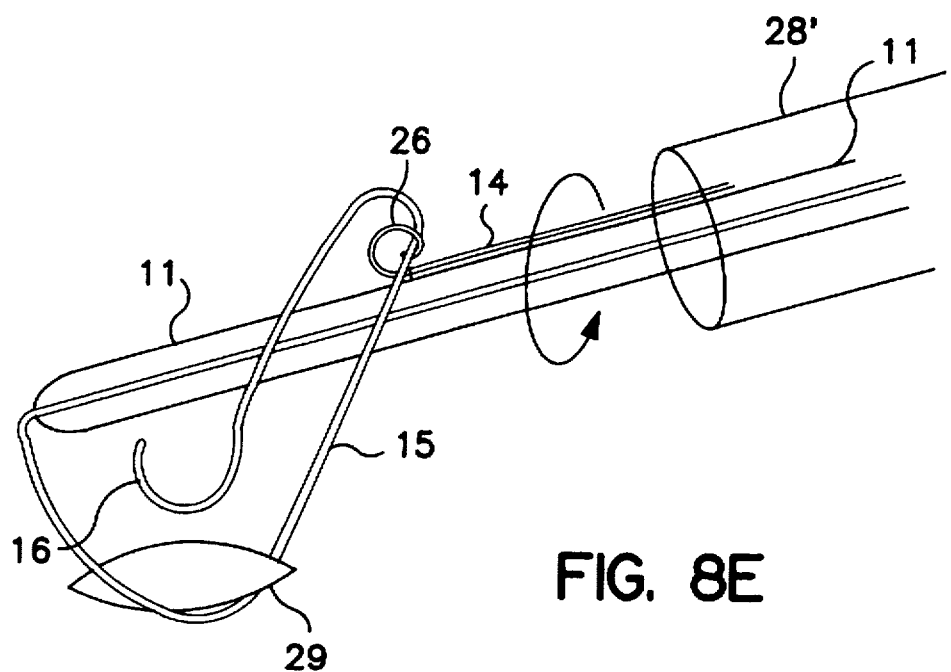

When properly used, a triangle is formed as shown in FIGS. 8D and 8E. The perimeter of the triangle is defined by the distal end (32) of the device (10), the portion of the ligature (15) entering the tissue, and the portion of the ligature (15) exiting the tissue. As shown in FIG. 8D, the needle (16) is passed through the triangle by the grasper (27). Holding the ligature (15) in the curled hook (26), dramatically simplifies the passage of the needle (16) through the triangle. Once the needle (16) is through the triangle, the semi-rigid wire (14) is retracted back into the covered portion (12) of the groove (13) and hook (26) is eliminated.

Figure 8F:
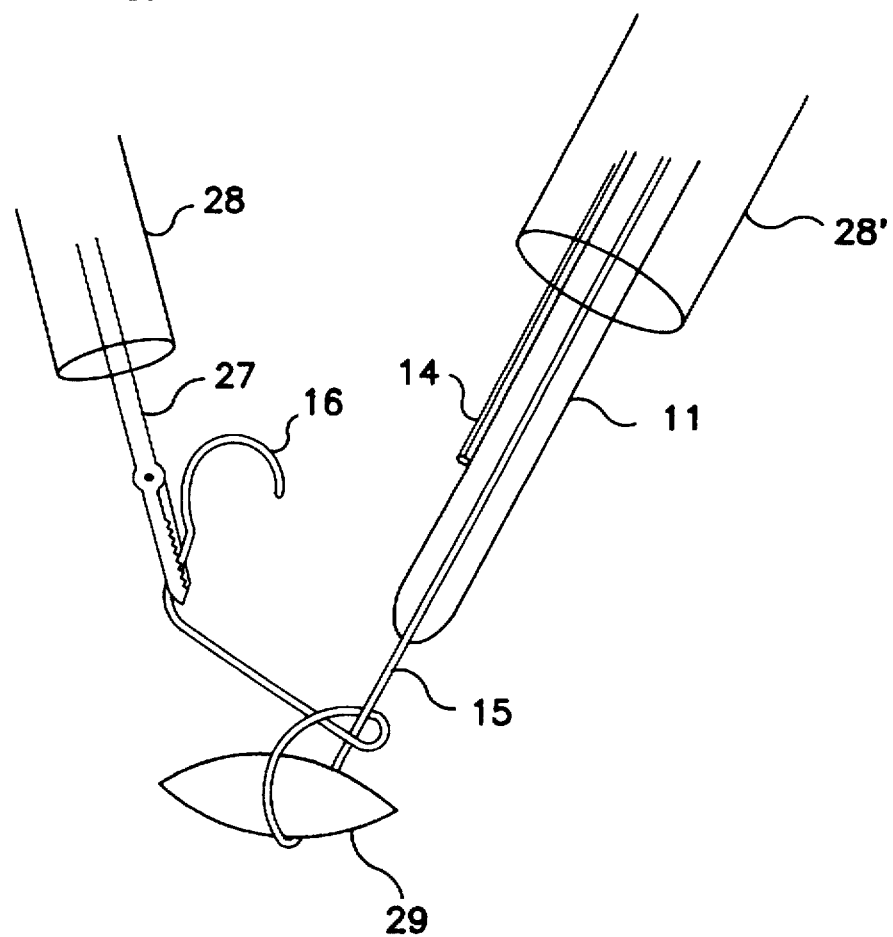

As shown in FIG. 8F, the knot is finalized using the grasper (27) by pulling the needle tightly through the triangle to form a knot. The distal end (32) of the device (10) can be used to push the knot into position. Multiple "throws" may be formed. A final throw in the opposite direction may be made, thus forming the locking throw of a surgeon's knot.

The same procedure can be accomplished using device (40) except, hook (33), is attached to the hollow needle holder (11) by a hinge (37). Hook (33) is activated according to the features of that embodiment.

While the invention has been described by the reference to specific embodiments, this was for purposes of illustration only and should not be construed to limit the spirit or the scope of the invention. For example, although the invention has been illustrated with respect to laparoscopic surgery, a person skilled in the art readily appreciates that it may be applied to many areas of endoscopic surgery.

I claim:

1. An intracorporeal ligature tying device, comprising:
   (a) a needle holder having a longitudinal channel running though the length of said needle holder, said needle holder having a proximal end and a distal end;
   (b) a longitudinal groove located on an outside surface of said needle holder, said groove terminating at a location on said needle holder prior to said distal end, at least a final portion of said groove being covered; and
   (c) a wire located in said groove, said wire being made from a memory material, said wire being slidably positioned within said groove so that in a retracted position, said wire terminates in said covered portion of said groove, and in an advanced position, an end of said wire extends beyond said covered portion of said groove and forms a hook to aid in tying a ligature within a patient's body.

2. The intracorporeal ligature tying device of claim 1 wherein, a needle and a ligature are passed through said longitudinal channel of said hollow needle holder so as to extend from the distal end of said hollow needle holder.

3. The intracorporeal ligature tying device of claim 2, wherein said distal end of said needle holder is shaped complementary to a cross section of said needle.

4. The intracorporeal ligature tying device of claim 2 further comprising, a push button attached to a proximal end of said wire in order to advance and retract said wire in said groove.

5. An intracorporeal ligature tying device, comprising:
   (a) a hollow needle holder having a proximal end, a distal end, and a groove running longitudinally along an outside surface of said hollow needle holder;
   (b) a wire longitudinally positioned within said groove; and
   (c) a hook movably attached to said outer surface of said hollow needle holder at a location proximate to said distal end of said hollow needle holder, said hook being connected to said wire so that said wire causes said hook to move into an operational position.

6. The intracorporeal ligature tying device of claim 5 wherein, said hook is attached to said outer surface of said hollow needle device by a hinge.

7. The intracorporeal ligature tying device of claim 5 further comprising, a push button attached to a proximal end of said wire in order to move said hook into said operational position.

* * * * *